United States Patent
Murai

(10) Patent No.: US 11,426,315 B2
(45) Date of Patent: *Aug. 30, 2022

(54) BED DEVICE

(71) Applicant: PARAMOUNT BED CO., LTD., Tokyo (JP)

(72) Inventor: Shinya Murai, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 35 days.

This patent is subject to a terminal disclaimer.

(21) Appl. No.: 17/119,532

(22) Filed: Dec. 11, 2020

(65) Prior Publication Data
US 2021/0093496 A1 Apr. 1, 2021

Related U.S. Application Data

(63) Continuation of application No. 16/580,007, filed on Sep. 24, 2019, now Pat. No. 10,893,992, which is a
(Continued)

(30) Foreign Application Priority Data

Nov. 22, 2011 (JP) .................................. 2011-254527

(51) Int. Cl.
A61G 7/018 (2006.01)
A47C 20/04 (2006.01)
(Continued)

(52) U.S. Cl.
CPC .............. A61G 7/018 (2013.01); A47C 20/04 (2013.01); A47C 31/008 (2013.01);
(Continued)

(58) Field of Classification Search
None
See application file for complete search history.

(56) References Cited

U.S. PATENT DOCUMENTS 3,578,379 A * 5/1971 Taylor ................ A47C 1/03211
297/316
3,839,753 A 10/1974 Benoit et al.
(Continued)

FOREIGN PATENT DOCUMENTS

CA 2239121 A1 * 6/1997 ......... A61G 7/05776
CA 2239121 C * 1/2006 ......... A61G 7/05776
(Continued)

OTHER PUBLICATIONS

European Search Report dated Jun. 10, 2015 issued in related Application No. 12850916.3.
(Continued)

Primary Examiner — Fekadeselassie Girma
(74) Attorney, Agent, or Firm — Birch, Stewart, Kolasch & Birch, LLP

(57) ABSTRACT

A bed device includes: an operation section that receives an operation input; a controller that controls a movement of the bed in accordance with the operation input; a detector that detects a position of a patient on the bed; and, a limitation table that stores a limitation area set on the bed in association with a limitation content, wherein when the position of the patient detected by the detector is included in the limitation area, the limitation content is read out from the limitation table so as to control the controller in accordance with the limitation content. With this configuration, it is possible to provide a higher safety bed device which can not only notify the danger based on the bed movement but also limit the movement of the bed in accordance with the status of the patient or the bed device.

16 Claims, 9 Drawing Sheets

Related U.S. Application Data continuation of application No. 16/143,848, filed on Sep. 27, 2018, now Pat. No. 10,463,552, which is a continuation of application No. 15/337,035, filed on Oct. 28, 2016, now Pat. No. 10,111,791, which is a continuation of application No. 14/918,996, filed on Oct. 21, 2015, now Pat. No. 9,504,619, which is a continuation of application No. 14/359,613, filed as application No. PCT/JP2012/079948 on Nov. 19, 2012, now Pat. No. 9,198,815.

(51) Int. Cl.
*A47C 31/00* (2006.01)
*A61B 5/11* (2006.01)
*A61G 7/015* (2006.01)
*A61G 7/00* (2006.01)
*A61G 7/012* (2006.01)
*A61G 7/057* (2006.01)
*G08B 3/10* (2006.01)
*G08B 5/22* (2006.01)
*G08B 21/02* (2006.01)

(52) U.S. Cl.
CPC ............ *A61B 5/1115* (2013.01); *A61G 7/001* (2013.01); *A61G 7/012* (2013.01); *A61G 7/015* (2013.01); *A61G 7/05769* (2013.01); *G08B 3/10* (2013.01); *G08B 5/22* (2013.01); *A61G 2203/12* (2013.01); *A61G 2203/16* (2013.01); *A61G 2203/20* (2013.01); *A61G 2203/32* (2013.01); *A61G 2203/34* (2013.01); *A61G 2203/42* (2013.01); *A61G 2203/46* (2013.01); *A61G 2203/70* (2013.01); *A61G 2203/726* (2013.01); *G08B 21/02* (2013.01)

(56) References Cited

U.S. PATENT DOCUMENTS

| | | | |
|---|---|---|---|
| 3,858,927 A | 1/1975 | Sutton | |
| 3,919,540 A | 11/1975 | Burst et al. | |
| 4,534,077 A | 8/1985 | Martin | |
| 4,807,558 A | 2/1989 | Swersey | |
| 5,153,586 A | 10/1992 | Fuller | |
| 5,161,158 A | 11/1992 | Chakravarty et al. | |
| 5,299,660 A | 4/1994 | Farmer | |
| 5,353,012 A | 10/1994 | Barham et al. | |
| 6,154,900 A | 12/2000 | Shaw | |
| 6,208,250 B1 | 3/2001 | Dixon et al. | |
| 6,362,725 B1 | 3/2002 | Ulrich et al. | |
| 6,772,456 B2 | 8/2004 | Votel | |
| 7,089,612 B2 | 8/2006 | Rocher et al. | |
| 7,472,437 B2 | 1/2009 | Riley et al. | |
| 7,676,862 B2 | 3/2010 | Poulos et al. | |
| 7,916,036 B1 | 3/2011 | Pope et al. | |
| 8,249,457 B2 | 8/2012 | Ruch et al. | |
| 8,347,429 B1 | 1/2013 | Hawkins | |
| 8,745,779 B2 | 6/2014 | Roberg | |
| 8,959,681 B2 | 2/2015 | Richards | |
| 9,009,893 B2 | 4/2015 | Kramer et al. | |
| 9,198,815 B2 | 12/2015 | Murai | |
| 9,504,619 B2 | 11/2016 | Murai | |
| 9,517,171 B2 | 12/2016 | Anderson et al. | |
| 10,064,784 B2 | 9/2018 | Rawls-Meehan | |
| 10,463,552 B2* | 11/2019 | Murai | A61G 7/015 |
| 10,893,992 B2* | 1/2021 | Murai | G08B 5/22 |
| 2002/0029418 A1 | 3/2002 | Votel | |
| 2002/0109610 A1 | 8/2002 | Katz | |
| 2002/0183979 A1 | 12/2002 | Wildman | |
| 2002/0196148 A1 | 12/2002 | Nunome | |
| 2004/0133982 A1* | 7/2004 | Horitani | A47C 20/041 |
| | | | 5/616 |
| 2005/0035862 A1 | 2/2005 | Wildman et al. | |
| 2005/0077859 A1* | 4/2005 | Nagaoka | A61G 7/018 |
| | | | 318/625 |
| 2006/0010601 A1 | 1/2006 | Riley et al. | |
| 2006/0028350 A1 | 2/2006 | Bhai | |
| 2006/0152378 A1 | 7/2006 | Lokhorst et al. | |
| 2007/0008156 A1 | 1/2007 | Ueda et al. | |
| 2007/0157385 A1 | 6/2007 | Lemire et al. | |
| 2007/0163045 A1 | 7/2007 | Becker et al. | |
| 2007/0169268 A1 | 7/2007 | Lemire et al. | |
| 2007/0288263 A1 | 12/2007 | Rodgers | |
| 2007/0296600 A1 | 12/2007 | Dixon et al. | |
| 2008/0071200 A1 | 3/2008 | Rawls-Meehan | |
| 2008/0169931 A1 | 7/2008 | Gentry et al. | |
| 2008/0195776 A1* | 8/2008 | Jensen | H04L 12/40006 |
| | | | 710/61 |
| 2008/0204254 A1 | 8/2008 | Kazuno | |
| 2008/0235872 A1 | 10/2008 | Newkirk et al. | |
| 2008/0281238 A1 | 11/2008 | Oohashi et al. | |
| 2009/0013474 A1 | 1/2009 | Gootee, Sr. | |
| 2009/0044334 A1 | 2/2009 | Parsell et al. | |
| 2009/0063183 A1 | 3/2009 | Mcneely et al. | |
| 2009/0100599 A1 | 4/2009 | Rawls-Meehan | |
| 2009/0119843 A1 | 5/2009 | Rodgers et al. | |
| 2009/0151074 A1* | 6/2009 | Nagaoka | A47C 20/08 |
| | | | 5/616 |
| 2009/0175421 A1 | 7/2009 | Gross et al. | |
| 2010/0052682 A1 | 3/2010 | Mueller | |
| 2010/0182153 A1 | 7/2010 | Jensen | |
| 2010/0201507 A1 | 8/2010 | Rao et al. | |
| 2010/0231421 A1 | 9/2010 | Rawls-Meehan | |
| 2010/0241321 A1 | 9/2010 | Luka et al. | |
| 2011/0208541 A1* | 8/2011 | Wilson | A61G 7/0527 |
| | | | 705/2 |
| 2011/0231996 A1 | 9/2011 | Lemire et al. | |
| 2012/0025991 A1 | 2/2012 | O'Keefe et al. | |
| 2012/0075464 A1 | 3/2012 | Derenne et al. | |
| 2012/0089419 A1 | 4/2012 | Huster et al. | |
| 2012/0137436 A1 | 6/2012 | Andrienko | |
| 2012/0140068 A1 | 6/2012 | Monroe et al. | |
| 2012/0191038 A1 | 7/2012 | Gerber | |
| 2012/0212582 A1 | 8/2012 | Deutsch | |
| 2013/0127620 A1 | 5/2013 | Siebers et al. | |
| 2013/0281804 A1 | 10/2013 | Lee et al. | |
| 2014/0104404 A1 | 4/2014 | Locke et al. | |
| 2014/0320290 A1 | 10/2014 | Reeder et al. | |
| 2014/0325760 A1 | 11/2014 | Murai | |
| 2016/0140307 A1 | 5/2016 | Brosnan et al. | |
| 2016/0140827 A1 | 5/2016 | Derenne et al. | |
| 2016/0143796 A1 | 5/2016 | Jordan et al. | |
| 2016/0183864 A1 | 6/2016 | Kusens et al. | |
| 2016/0314672 A1 | 10/2016 | Wiggermann et al. | |
| 2017/0143566 A1 | 5/2017 | Elku et al. | |
| 2017/0360212 A1* | 12/2017 | Rawls-Meehan | A47C 27/14 |
| 2019/0151145 A1 | 5/2019 | Campos et al. | |
| 2020/0016016 A1* | 1/2020 | Murai | A61G 7/012 |
| 2021/0093496 A1* | 4/2021 | Murai | A61G 7/015 |

FOREIGN PATENT DOCUMENTS

| | | | | |
|---|---|---|---|---|
| CA | 2711672 A1 * | 7/2009 | ........... | B01D 15/206 |
| EP | 1975750 A2 | 10/2008 | | |
| JP | 07163622 A * | 6/1995 | | |
| JP | H07-163622 A | 6/1995 | | |
| JP | H085301 B2 * | 1/1996 | ........... | B60G 17/015 |
| JP | H10-5286 A | 1/1998 | | |
| JP | 2000-157603 A | 6/2000 | | |
| JP | 2004-159805 A | 6/2004 | | |
| JP | 2004-159807 A | 6/2004 | | |
| JP | 2005-027735 A | 2/2005 | | |
| JP | 2005-177313 A | 7/2005 | | |
| JP | 2007-54262 A | 3/2007 | | |
| JP | 2007-252715 A | 10/2007 | | |
| JP | 2008-206869 A | 9/2008 | | |
| JP | 2011-156141 A | 8/2011 | | |
| JP | 2011-189137 A | 9/2011 | | |
| WO | WO 00/51541 A2 | 9/2000 | | |

(56) References Cited

FOREIGN PATENT DOCUMENTS

| WO | WO 01/70167 A2 | 9/2001 |
| WO | WO 2007/056342 A2 | 5/2007 |
| WO | WO 2009/124397 A2 | 10/2009 |

OTHER PUBLICATIONS

Extended European Search Report dated Oct. 15, 2015, issued in related Application No. 12850916.3.
European Search Report issued in corresponding European Application No. 12850916.3 dated Dec. 11, 2017.
Japanese Notification of Reasons for Refusal issued in corresponding Japanese Application No. 2016-248443 dated Feb. 20, 2018.
Notification of Reasons for Refusal issued in corresponding Japanese Patent Application No. 2016-248443 dated Dec. 5, 2017.
U.S. Appl. No. 16/580,007, filed Sep. 24, 2019.
U.S. Appl. No. 16/143,848, filed Sep. 27, 2018.
U.S. Appl. No. 15/337,035, filed Oct. 28, 2016.
U.S. Appl. No. 14/918,996, filed Oct. 21, 2015.
U.S. Appl. No. 14/359,613, filed May 21, 2014.

\* cited by examiner

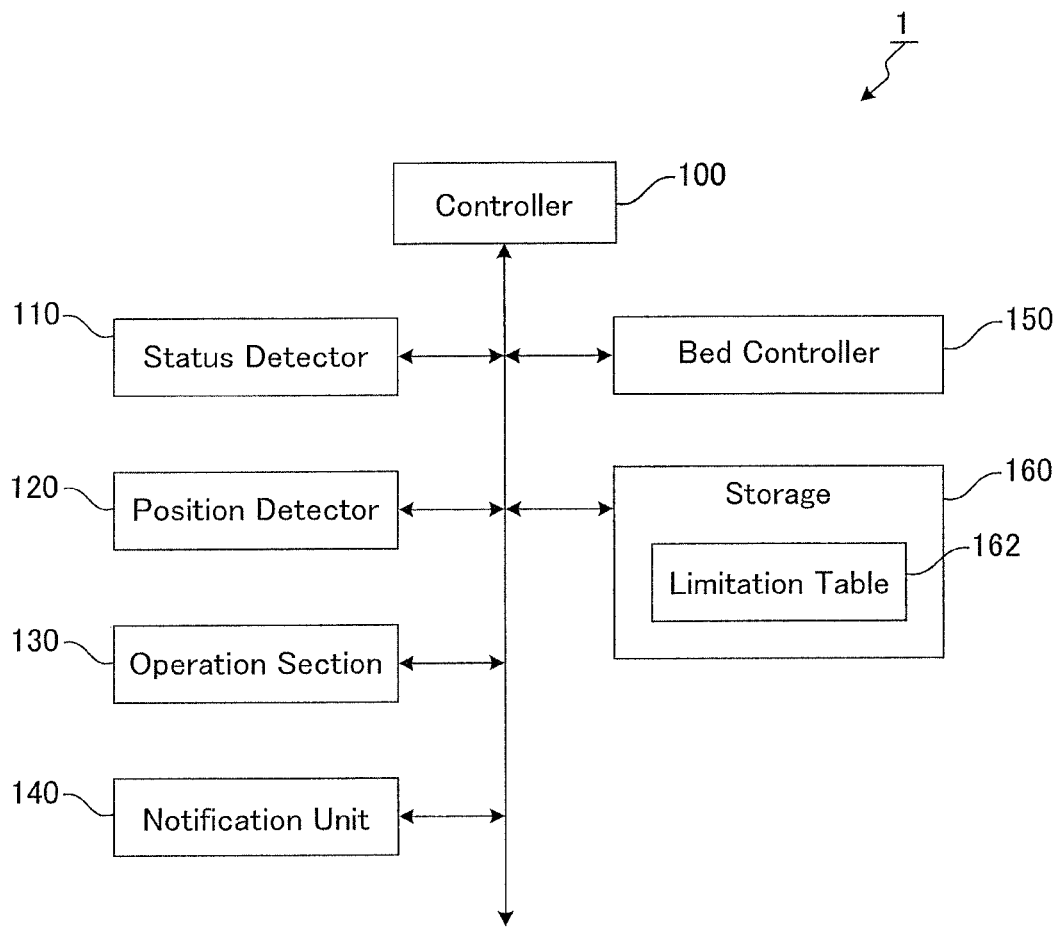

| Bed Mode | Bed Operation Content | Notifying Operation | Bed Control |
|---|---|---|---|
| Edge-sitting Mode | Knee Rise Operation | ON | Suspended |
| Transfer Mode | Back Rise Operation | ON | Suspended |
| ⋮ | ⋮ | ⋮ | ⋮ |

| Bed Status | Bed Function | Bed Limitation Content |
|---|---|---|
| Back Rise angle >5 deg. | Rolling Function | Perform notifying process without rolling function |
| ⋮ | ⋮ | ⋮ |
| Patient is detected in limitation area | Rolling Function | Rolling function is not performed |
| ⋮ | ⋮ | ⋮ |

BED DEVICE

CROSS-REFERENCE TO RELATED APPLICATIONS

This application is a Continuation of co-pending U.S. application Ser. No. 16/580,007, filed on Sep. 24, 2019, which is a Continuation of U.S. application Ser. No. 16/143,848, filed on Sep. 27, 2018 (now U.S. Pat. No. 10,463,552 issued on Nov. 5, 2019), which is a Continuation of U.S. application Ser. No. 15/337,035, filed on Oct. 28, 2016 (now U.S. Pat. No. 10,111,791 issued on Oct. 30, 2018), which is a Continuation of U.S. application Ser. No. 14/918,996, filed on Oct. 21, 2015 (now U.S. Pat. No. 9,504,619 issued on Nov. 29, 2016), which a Continuation of U.S. application Ser. No. 14/359,613, filed on May 21, 2014 (now U.S. Pat. No. 9,198,815 issued on Dec. 1, 2015), which is the National Phase of PCT/JP2012/079948 filed on Nov. 19, 2012, which claims priority under 35 U.S.C. § 119(a) to Patent Application No. 2011-254527 filed in Japan on Nov. 22, 2011, all of which are hereby expressly incorporated by reference into the present application.

TECHNICAL FIELD

The present invention relates to a bed device.

BACKGROUND ART

The bed device is able to realize various kinds of operations such as back rise and knee rise in bed mode by operating the actuators connected to the bottom part so as to change mode into a condition suitable for the patient and change the shape of the bottom part in conformity with the patient's posture.

Herein, for the bed device, there is a known function, which, in advance, prohibits risky control against the patient (bed control prohibiting function or the like). In use of the bed control prohibiting function, when a predetermined control has been prohibited in advance, if the person (operator) who operates the bed device performs the predetermined control it is possible to avoid, for example a dangerous operation that would cause the patient to fall from the bed.

There has been another known invention, by which the position of the patient on the bed device is detected so as to give an alarm when the patient stays in a dangerous position (e.g., see Patent Document 1). This configuration makes it possible to notify the operator when the patient is staying at a hazardous position where the patient would fall from the bed device or be strongly caught into the bed.

PRIOR ART DOCUMENT

Patent Document

Patent Document 1: Japanese Patent Application Laid-open 2008-206869

SUMMARY OF THE INVENTION

Problems to be Solved by the Invention

However, even if an alarm is raised when the patient is staying in the hazardous position (position with a high risk), the operator needs to manually stop the operation and/or adjust the position of the patient. As a result, when operating the bed device the operator is demanded to always pay attention to the patient and the bed device, which makes heavy burden.

In particular, a risk that can be expected beforehand such as a case, for example where the patient gets caught in the bed at the time of a back rise operation, would be well, the operator, however, has to always pay attention to the bed device to deal with risks that the operator cannot expect. This makes especially heavy burden to the operator.

Further, the conventional bed devices have been mostly operated in a hospital or nursing home by those skilled in controlling the bed, such as medical personnel and nursing home personnel. However, thanks to recent spread of in-home care, the bed devices have become more used at home. In such cases, the operator is a person such as a family member of the patient, who is not familiar with the control of the bed device. Accordingly, in order to assure safety, the operator needs to pay attention to the patient and the bed device, which is a heavy burden. Moreover, it takes a longer time for the unskilled to stop the operation compared to the case in which the skilled operates, hence posing the problem of increased risk.

In view of the problems described above, it is therefore an object of the present invention to provide a bed device which not only notifies the danger of the bed operation but also provides higher measures that limit the operation of the bed, in accordance with a state of the patient or bed device in accordance with a state of the patient or a state of the bed device.

Means for Solving the Problems

In view of the above problems, a bed device of the present invention includes:
an operation section that receives an operation input;
a controller that controls a movement of the bed in accordance with the operation input;
a detector that detects a position of a patient on the bed; and,
a limitation table that stores a limitation area set on the bed in association with a limitation content, wherein when the position of the patient detected by the detector is included in the limitation area, the limitation content is read out from the limitation table so as to control the controller in accordance with the limitation content.

The bed device of the present invention is characterized in that an operation content of the bed is additionally stored in relational manner in the limitation table, and
the limitation content is read out from the limitation table, based on the operation input and the patient position detected by the detector.

A bed device of the present invention includes:
an operation section that receives an operation input;
a controller that controls the movement of the bed in accordance with the operation input; and,
a limitation table that stores a bed mode for the controller to cause the bed to move so as to take a predetermined form and limitation contents in a relational manner, wherein when the operation input is entered from the operation section, the limitation content corresponding to the operation input and the bed mode is read out from the limitation table, and the controller is controlled based on the limitation content.

The bed device of the present invention is characterized in that the bed mode is to operate an edge-sitting mode.

The bed device of the present invention is characterized in that the limitation content is to perform a control of suspending the movement of the bed.

The bed device of the present invention further includes a notifying means for notifying an operator of an alert, and is characterized in that the limitation content is to notify the operator of the alert by means of the notifying means.

Advantages of the Invention

According to the present invention, a bed device includes: an operation section that receives an operation input; a controller that controls a movement of the bed in accordance with the operation input; a detector that detects a position of a patient on the bed; and, a limitation table that stores a limitation area set on the bed in association with a limitation content, and is characterized in that when the position of the patient detected by the detector is included in the limitation area, the limitation content is read out from the limitation table so as to control the controller in accordance with the limitation content. That is, it is possible to read out limitation content and implement control of the operation of the bed device appropriately, depending on the position of the patient.

BRIEF DESCRIPTION OF DRAWINGS

FIG. 2 A diagram for illustrating the functional configuration of the bed device in the first embodiment.
FIG. 3 A diagram for illustrating the table configuration of a limitation table in the first embodiment.

MODE FOR CARRYING OUT THE INVENTION

Hereinbelow, the best mode for carrying out the present invention will be described with reference to the drawings. The following embodiments of the present invention are mere examples, and the detecting method and other methods should not be definitely limited to the description of the embodiments.

1. The First Embodiment 1.1 Explanation of Device Profile

Figure 1:
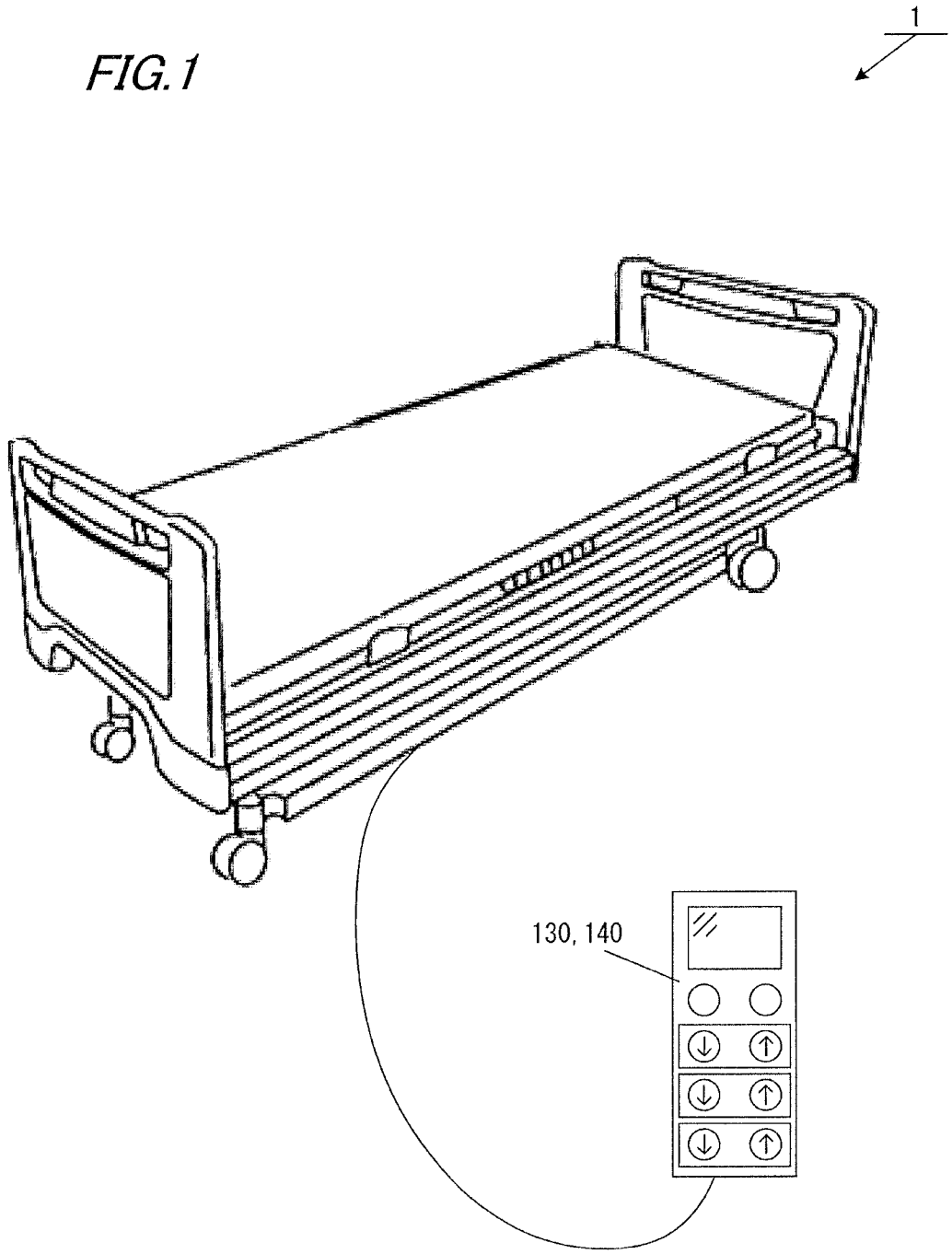
FIG. 1 A diagram for illustrating the overall configuration of a bed device in the present embodiment.

To begin with, the overall configuration of a bed device to which the present invention is applied will be described with reference to FIG. 1. FIG. 1 is a diagram for illustrating the overview of a bed device 1 in the present embodiment. Bed device 1 is one that can implement various operations such as back rise, leg rise, and knee rise when the bottom part is actuated. A mattress is mounted on the bed body.

An operation section 130 for controlling the operation of the bed device is connected. The operator controls the operation of the bed device by operating the operation section 130. Operation section 130 also includes a notification unit 140 for displaying the status of the bed device.

1.2 Functional Configuration

Next, the functional configuration of bed device 1 will be described with reference to FIG. 2. In bed device 1, connected to a controller 100 are a status detector 110, a position detector 120, the operation section 130, a notification unit 140, a bed controller 150 and a storage 160, as shown in FIG. 2.

Controller 100 is a functional unit for controlling bed device 1 as a whole. Controller 100 implements diverse functions by reading and executing various programs stored in storage 160. Here, controller 100 is formed of, for example a CPU (Central Process Unit) and the like.

Status detector 110 is a functional unit for detecting various states in bed device 1. For example, the detector detects the states by detecting the state of the pressure sensor and detecting the operational signals of the actuators. Herein, the states detected may include various states such as, for example, the back rise angle of the bed, the leg lowering angle and bed mode.

Herein, bed mode in the present embodiment represents the operational mode of the bed. As the bed mode, various modes are prepared. Examples include an edge sitting mode that is suitable for the patient to sit on the edge of the bed device. When the edge sitting mode is selected and implemented by the operation section, the bottom part of the bed device operate to be horizontal so as to allow the patient to sit on the edge while the height of the bed is also adjusted. Further, when an air mattress is connected, the area where the patient sits is deflated so that the patient can take a stable sitting position. That is, in accordance with the selected bed mode the bed device automatically performs the back rise function, the leg lowering function, adjustment of the air mattress and the like, and achieves movement control that enables all the necessary operations answering the user's purpose, to be implemented by a single operation.

Position detector 120 is a functional unit for detecting the position of the patient on the bed device. Position detector 120 may detect the area where the patient stays or the center of gravity of the patient. As the detecting method, the position of the patient may be calculated, for example, from the measurement values of the load sensors arranged in the bed device (bed body), or the portion of the patient may be detected by means of a pressure sensor, or may be detected using an infrared sensor or a temperature sensor. That is, the position detector is a functional unit for detecting where in the bed device (e.g. on the mattress) the patient is located.

Operation section 130 is a functional unit that allows the operator to operate bed device 1. For example, the operation section is connected wiredly or wirelessly to the control unit of bed device 1, or is directly installed in the bed device. Instructions for an operation from the operator are input through operation buttons provided in operation section 130. Based on the input instructions for the operation, bed device 1 operates. As operation section 130, a publicly known input unit such as key input, touch panel, and voice input may and should be used.

Notification unit 140 is a functional unit that notifies the status of bed device 1, notifies operation content and gives a warning to predetermined operations. Example of notification unit 140 may be a publickly known notification unit including a display unit such as a liquid crystal panel, a sound output unit such as a speaker. The notification unit may include a configuration that outputs an alarm sound (warning sound).

Bed controller 150 is a functional unit for controlling the operation of bed device 1. For example, the bed controller is a functional unit that performs control of back rise operation and the like by controlling the actuators connected to bottom parts of the bed body.

Storage 160 is a functional unit that stores various programs, and various data, required to operate bed device 1. Storage 160 is configured of semiconductor memories, HDD (Hard Disk Drive) and the like, for example.

Storage 160 also stores a limitation table 162. FIG. 3 shows one example of limitation table 162. As shown in FIG. 3, limitation table 162 is recorded with a limitation area setting (e.g., "R12"), bed control content (e.g., "knee rise operation"), limitation content (in the present embodiment, notifying operation (for example, "ON" and bed operation (e.g., "Suspended").

Figure 4:
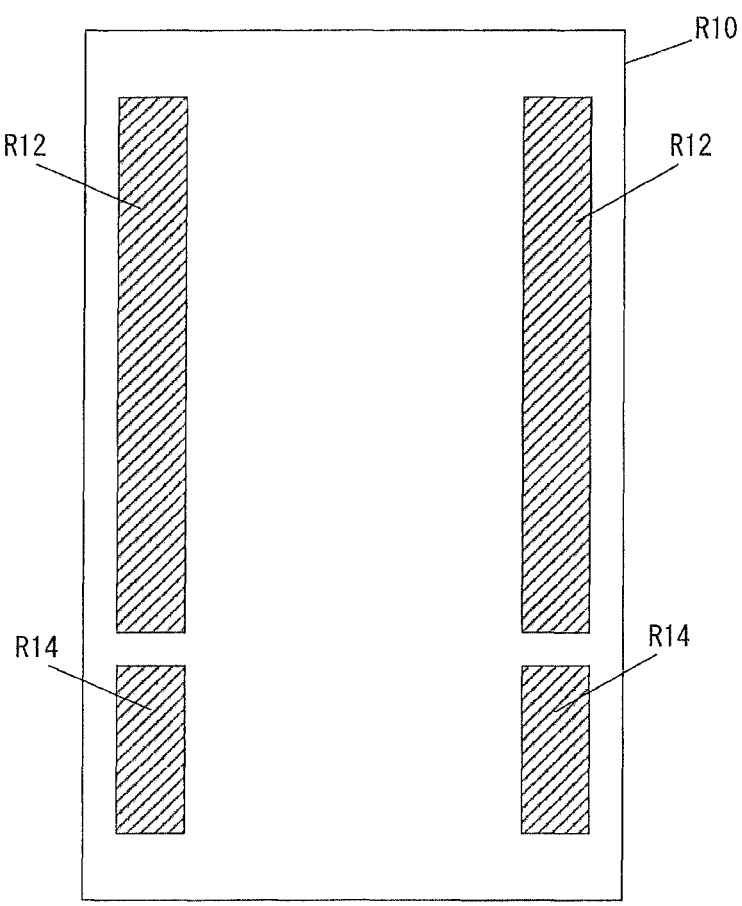
FIG. 4 A diagram for illustrating limited areas in the first embodiment.

Herein, the limitation areas indicate the areas defined in the bed device (mattress). Depending on detection of the patient in the limitation areas, various limiting processes are implemented. For example, as shown in FIG. 4, predetermined areas on the bed device (mattress) are designated as the limitation areas. For example, area R12 and area R14 are designated as the limitation areas.

In the present embodiment, as a method of designating limitation areas, XY coordinates may be defined on the bed device (mattress) so as to designate the predetermined areas in the XY coordinates as the limitation areas. Herein, it is also possible to designate limitation areas every bottom part, for example. It is also possible to set up based on detection of a load equal to or greater than a predetermined proportion, from the pressure sensor. That is, any methods capable of detecting the position of the patient can be used as the method of designating limitation areas.

1.3. Process Flow

Figure 5:
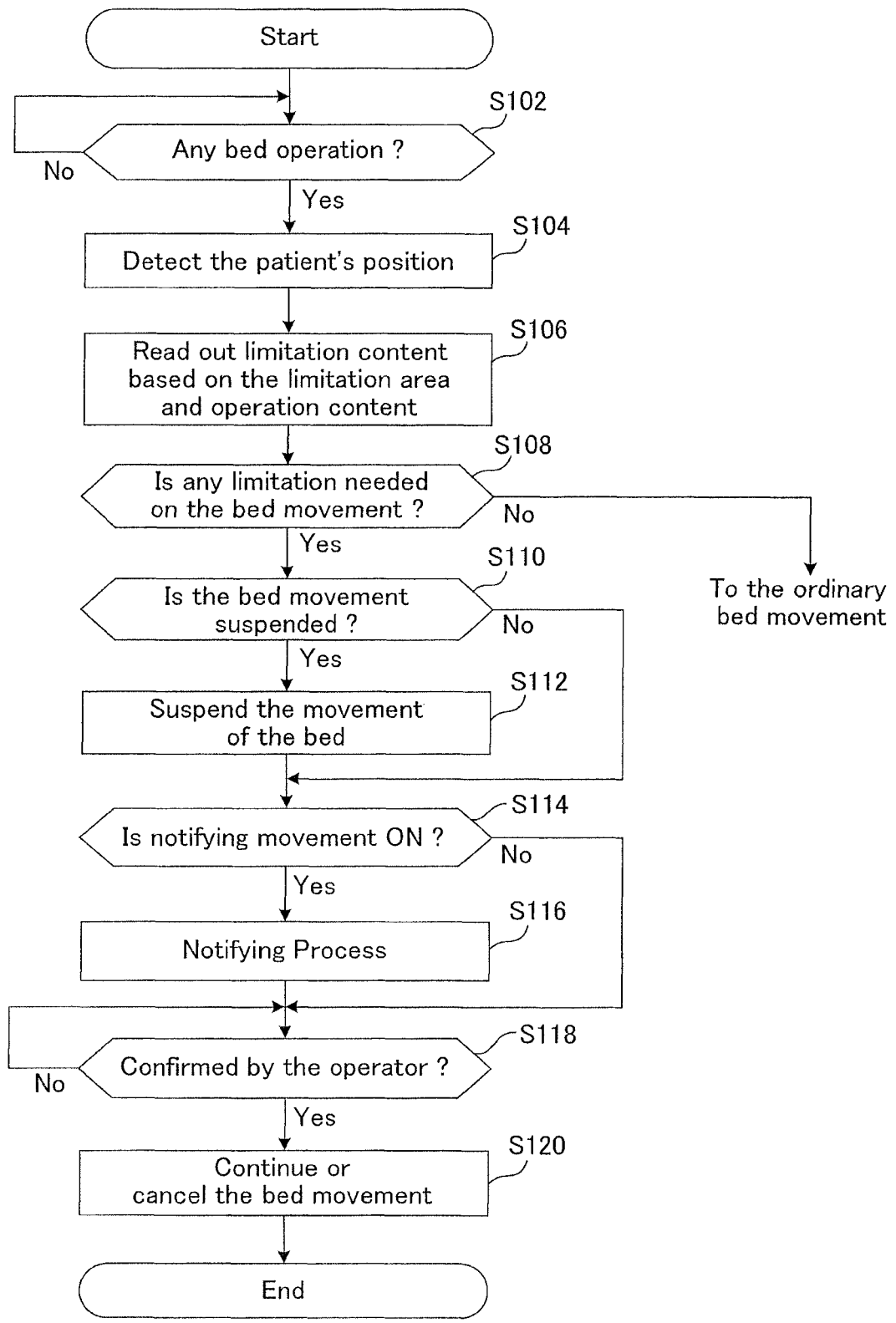
FIG. 5 An operational flow for illustrating the processing of the first embodiment.

Next, the processing flow of the present embodiment will be described using the drawings. FIG. 5 shows a flow of the process in the present embodiment.

To begin with, it is determined whether any bed control has been made (Step S102). If the operator has made a bed operation (Step S102; Yes), the position of the patient is detected (Step S104). The patient position is detected by position detector 120.

Subsequently, in accordance with the patient position detected at Step S104 and the bed operation made by the operator, limitation content is read out from limitation table 162 (Step S106). At this stage, when it is determined that no limitation on bed movement is needed (Step S108; No), the ordinary bed operation is implemented.

On the other hand, when it is determined that a limitation on bed movement is needed (Step S108; Yes), the limiting process on bed movement is implemented. Specifically, the limitation content with respect to the bed movement corresponding to the limitation areas and the bed operation content is read out from limitation table 162 and judged. First, it is determined whether or not the bed operation is "suspended" (Step S110). If the bed operation is "suspended", the operation of the bed is stopped temporarily (Step S110; Yes→Step S112).

Subsequently, the notifying operation is "ON" (Step S114; Yes), the notifying process is implemented (Step S116). The notifying process indicates the process of displaying a warning on the display and/or outputting a warning sound (alarm sound), for example.

Thereafter, it is determined whether or not the operator has confirmed the notification (Step S118; Yes). At this stage, when the operator's confirmation has been detected (Step S118; Yes), the bed movement is continued or cancelled in accordance with the content of confirmation (Step S120).

As a result, after the operator's confirmation of the status of the patient, it is possible to continue the operation if the risk is determined to be low or to cancel the operation if the risk is determined to be high. During this, when the operation has been set to be suspended at Step S112, a high-risk operation is suspended, so that it is possible to offer a safer bed device.

1.4 Operational Examples

Figure 6:
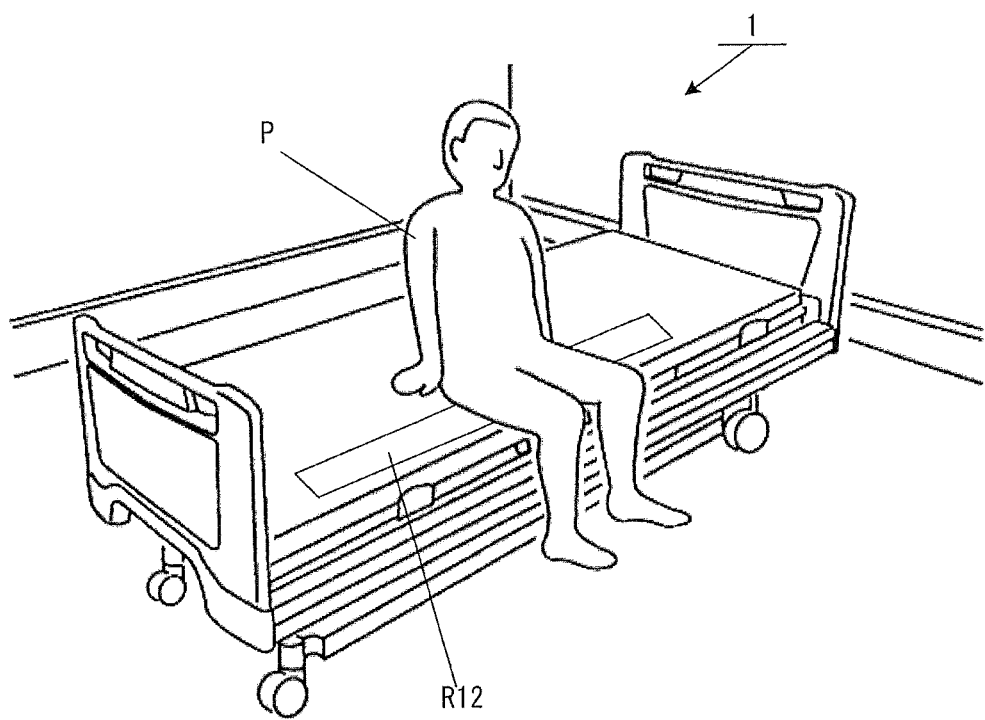
FIG. 6 A diagram for illustrating an operational example in the first embodiment.

Next, operational examples of the present embodiment will be described with reference to the drawings. FIG. 6 is a diagram showing a situation where a patient P is sitting on the edge portion in bed device 1. Since patient P is in the edge sitting position, the position of the patient is detected as area R12.

In this situation, if a "knee rise operation" is directed by the operator, there is a risk that patient P as is may fall from the bed device 1. For this reason, before implementing the leg rise operation, the bed movement is temporarily stopped (Step S112 in FIG. 5) and a notifying process is performed (Step S116 in FIG. 5).

FIG. 7(a) shows one example of a display screen W100 displayed in notification unit 140 in this state. In FIG. 7(a), a warning is displayed in an area R100 so as to ask the operator for confirmation of the movement. In this case, the operator takes measures such as shifting the patient' position so as to eliminate the risk of the patient falling, the operator selects the button displayed in an area R102 in order to continue the current bed operation.

On the other hand, when it is determined that there is a risk because patient P is staying in area R12, the operator selects the button displayed in area R104 for cancelling the bed operation. Here, it is also possible to produce an alarm sound in addition in order to notify the operator distinctly.

FIG. 7(b) shows another example of a display screen W110. For example, when suspension of bed operation has not been set while only the notifying operation has been set "ON", the notifying process is implemented while the bed continues to operate.

In this way, according to the present embodiment, it is possible to limit the operation of the bed device in accordance with the position of the patient on the bed device and the operation content of the bed made by the operator. For example, it is possible to suspend the movement of the bed device and/or implement a notifying process. As a result, it is possible to provide a bed device with a higher safety, which can limit the movement of the bed device in accordance with the position of the patient.

2. The Second Embodiment

Next, the second embodiment will be described. In the first embodiment, the bed movement is limited based on the position of the patient and the content of the operation of the bed. In the second embodiment, the bed movement is limited based on bed mode and content of the operation of the bed.

Figures 7, 8:
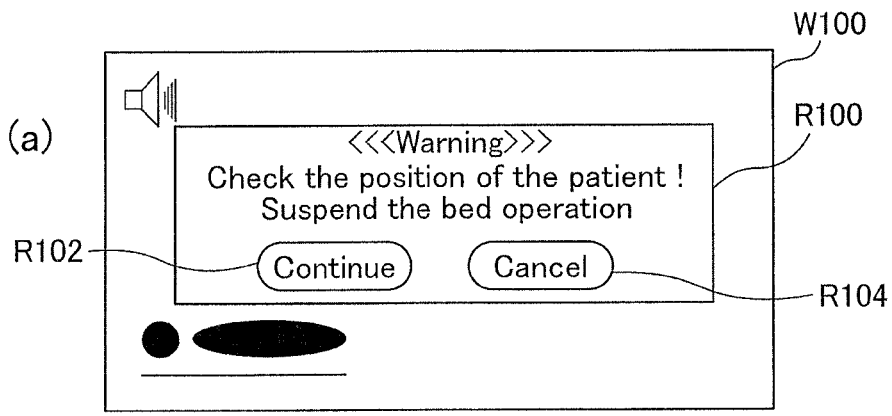
FIG. 7 A diagram for illustrating a notification example in the first embodiment.
FIG. 8 A diagram for illustrating the table configuration a limitation table in a second embodiment.

In the second embodiment, a limitation table 164 shown in FIG. 8 is stored instead of limitation table 162 described in the first embodiment.

Limitation table 164 in FIG. 8 has stored bed mode, bed operation content, notifying operation and bed control in a relational manner. That is, instead of the limitation area of limitation table 162 of the first embodiment, the bed mode is stored.

Bed mode indicates the movement mode when the bed moves. For example, the "edge sitting mode" is a mode suitable for the patient to take the edge sitting position.

Meanwhile, the bed device of the second embodiment has the same configuration as that of the bed device described in the first embodiment with FIG. 2, the description is omitted. Here, in the diagrams of functional blocks described in the first embodiment with FIG. 2, this embodiment is also allowed not to contain position detector 120.

Figure 9:
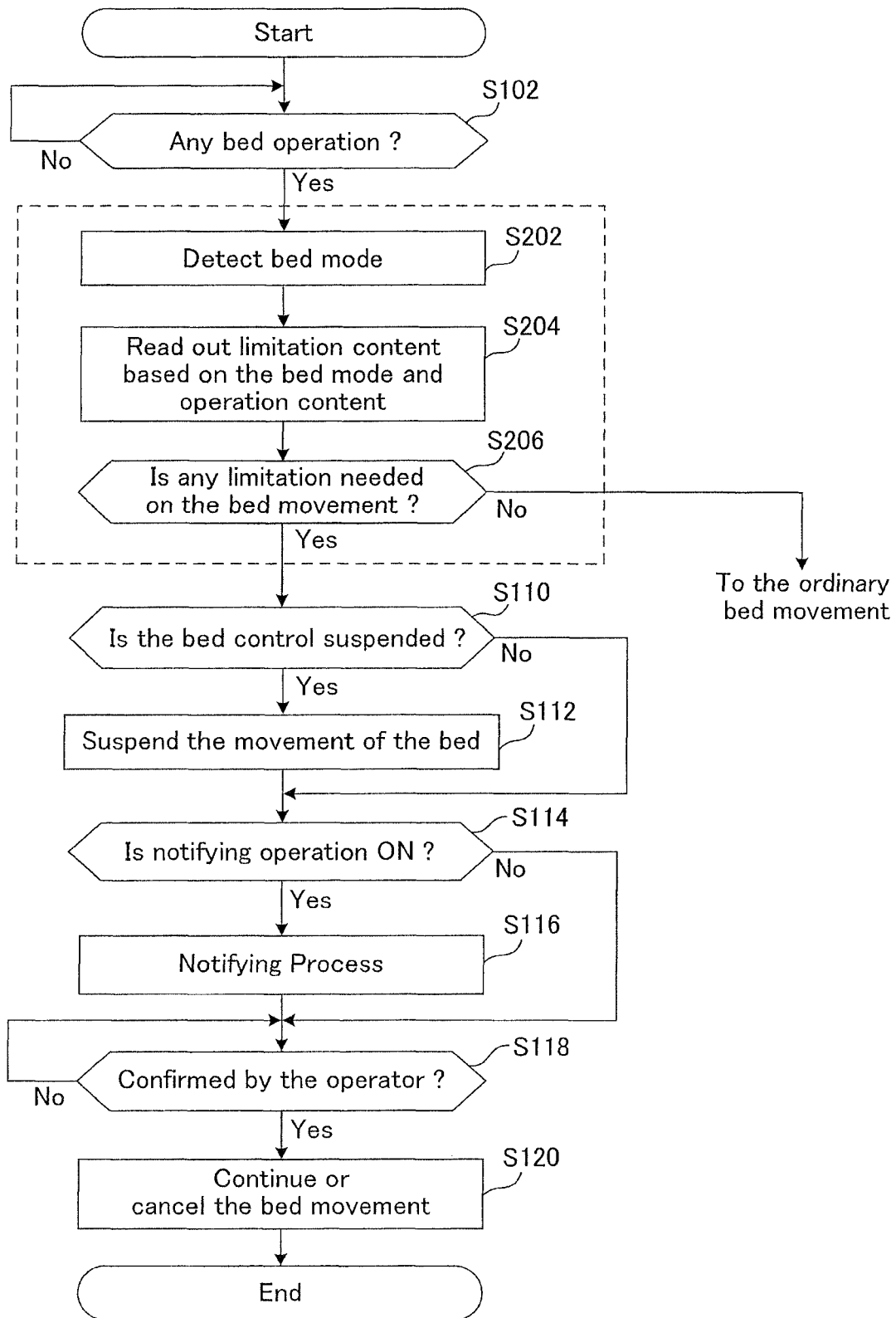
FIG. 9 An operational flow for illustrating the processing in the second embodiment.

FIG. 9 is a diagram for explaining the flow of processing in the present embodiment. The flow of the process in the present embodiment is the one described in the first embodiment with FIG. 5, in which Steps S104 to S108 are replaced by Steps S202 to S206. The other steps allotted with the same reference numerals are the same as those in the first embodiment, so that description is omitted.

First, when a bed operation is detected at Step S102, the current bed mode is detected (Step S202). Then, the limitation content associated with the detected bed mode and the operation content is read out from limitation table 164 (Step S204).

Here, when no limitation on bed operation is needed, the ordinary bed operation is implemented (Step S206; No). When limitation on the movement of the bed is needed, the process from Step S110 is implemented (Step S206; Yes).

In this way, according to the second embodiment, it is possible to limit the movement of the bed and perform the notifying process in accordance with the operation content and the bed mode. As a result, only the movement suited to the bed mode can be implemented, thus it is possible to provide a bed device with higher safety.

3. The Third Embodiment

Next, the third embodiment will be described. The third embodiment handles a case where the bed function is limited based on the status of the bed.

3.1 Configuration

First, the bed device in the present embodiment and the conditions of the air mattress and others will be described with FIG. 10.

The bed device includes a mat body 10 mounted on a base 30. Herein, mat body 10 is formed of a plurality of cells 14 arranged contiguously in the longitudinal direction. These cells are enfolded by a cover 12 of a top cover and a bottom cover, to form mat body 10.

Bed device 1 further includes a rolling portion 20. Rolling portion 20 includes side cells 22 and rolling cells 24, which are used to change the patient position.

Figures 10, 11:
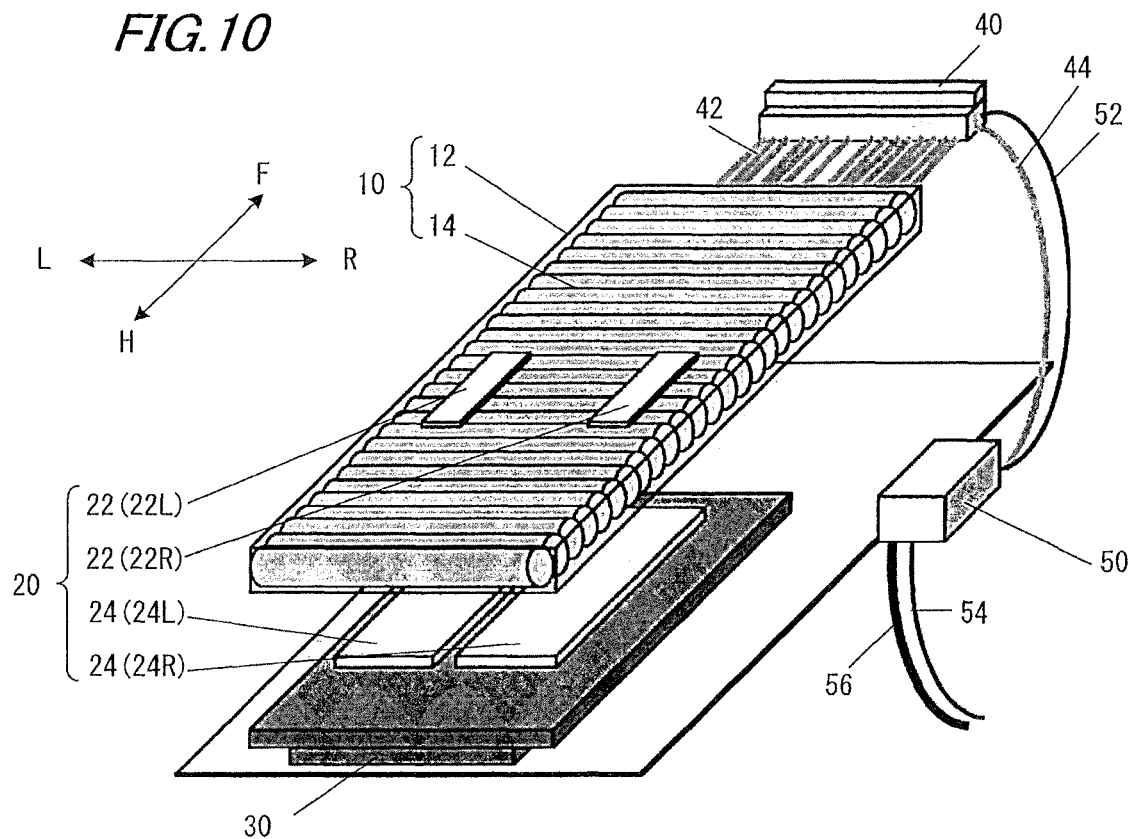
FIG. 10 A diagram for illustrating the configuration of a third embodiment.
FIG. 11 A diagram for illustrating the table configuration a limitation table in the third embodiment.

Herein, bed device 1 is used with the patient foot side oriented in the direction of F (to the controller 40 side) in FIG. 10 and the head side in the direction of H in FIG. 10. Accordingly, the R-direction in FIG. 10 is on the right side of the patient and the L-direction in FIG. 10 is on the left side.

Side cells 22 are formed of a side cell 22R on the right side and a side cell 22L on the left side. Rolling cells 24 are formed of a rolling cell 24R on the right side and a rolling cell 24L on the left side.

Connected to individual cells (cells 14, side cells 22, rolling cells 24) are air blow tubes 42 from controller 40. An air blow tube 44 from a pump unit 50 is connected to controller 40. Further, controller 40 and pump unit 50 are connected to each other by a control cable 52 so that various control signals are exchanged therebetween. Connected to pump unit 50 are a control cable 54 from without and a power cable 56 for driving the pump.

Individual cells 14 are separated into a plurality of branch groups, the cell of each branch group being connected to a common air blow tube 42 as a communication path. Air blow tube 42 is connected to a selector valve by way of an air blow tube connector. The selector valve is connected to pump unit 50 by way of the air blow tube. Thus, the movement of pump unit 50 and the selector valve inflates and deflates individual cells.

Similarly to the inflating and deflating movement of these cells 14, side cells 22 and rolling cells 24 are also connected to air blow tubes 42 and connected to selector valves via air blow tubes 42. The selector valves are connected to pump 50 via air blow tubes 44 so as to perform inflation and deflation.

Here, air blow tubes 42 as the communication paths may be constructed so that a single tube output from pump unit 50 is branched into the plurality of tubes connected to cells, or so that a plurality of tubes are output from pump unit 50. In other words, any configuration may be accepted as long as each cell can be made to take the same pressure value with others in making each cell communicate with others.

Subsequently, the functional configuration of the bed device in the third embodiment will be described. The bed device of the third embodiment has the same functional configuration as that of the first embodiment shown with FIG. 2 except in that a limitation table 166 shown in FIG. 11 is stored instead of limitation table 162 described in the first embodiment.

Limitation table 166 in FIG. 11 stores bed status (e.g., "back rise angle >5 deg."), bed functionality (e.g., "rolling function") and bed limitation content (e.g., "perform a notifying process without implementation of the rolling function), in a relational manner.

The bed status includes the states of the bed device and mattress (e.g., inflated and deflated conditions of cells 14 in the present embodiment), the state of the patient staying in bed or getting out of bed, the position of the patient, the state of the bottom parts of the bed; among these the aftermentioned conditions for determination when the bed functionality is limited, are stored.

As the bed functionality, functions for performing various kinds of movements of the bed device are stored. For example, the rolling function is a function to change the position of the patient by inflating and deflating rolling cell 24L and rolling cell 24R alternately.

Bed limitation content is information storing what limitation should be actually imposed on the function and movement of the bed device. The content may be stored separately for each movement as in the first embodiment or may be stored comprehensively as in this embodiment.

Figure 12:
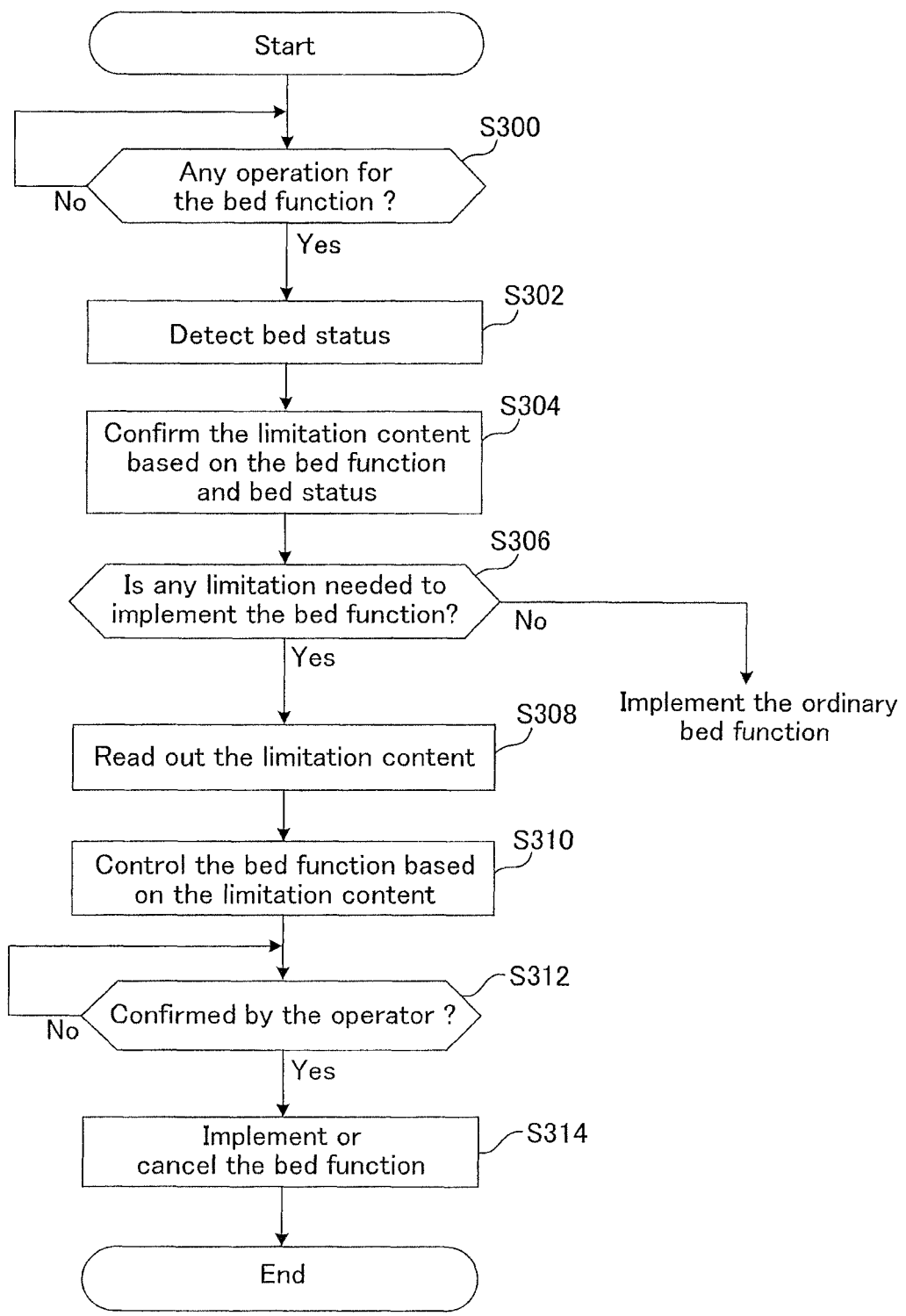
FIG. 12 An operational flow for illustrating the processing in the third embodiment.

FIG. 12 is a diagram for explaining the process flow in the present embodiment. To begin with, it is determined whether or not any user operation for a bed function has been made (Step S300). When an operation for some bed function has been made, the bed status is detected (Step S302).

At this stage, in detecting the bed status, various items are detected. Examples of the items include the angles of the bottom parts, the patient position, the internal pressure values of cells 14 in mattress body 10. Based on the detected conditions of the bed and the bed status detected at Step S300, the limitation content is confirmed from limitation table 166 (Step S304).

When no limitation is needed to implement the bed function, the ordinary bed function is implemented (Step S306; No). When a limitation is needed to implement the bed function, the limitation content is read out from limitation table 166 (Step S308). Here, when the limitation content has been already read out at Step S304, it is not necessary to implement Step S308.

Subsequently, based on the limitation content, the bed function is controlled (Step S310). For example, implementation of the bed function is suspended (or cancelled) while a notifying process is implemented for the user.

At this stage, when the operator enters confirmation (Step S312; Yes), the bed function is kept up and implemented or cancelled, based on the confirmed content.

In the above way, according to the present embodiment, when a bed function is implemented, it is possible to implement or cancel the bed function by detecting the current status of the bed device and based on the status of the bed device.

4. Variational Example

As the embodiment of this invention has been detailed with reference to the drawings, the specific configuration should not be limited to this embodiment. Designs and others that do not depart from the gist of this invention should also be included in the scope of claims.

Though the above embodiments were described on the assumption that the position detection of the patient is performed at the beginning, it is possible to detect at regular intervals of a predetermined period. That is, in the operation flow of FIG. 5, when it is determined that no limitation on the bed movement is needed (Step S108; No), the ordinary bed movement is implemented while the iteration process from Step S104 is implemented. As a result of this, it is possible to limit the bed movement and/or perform a notifying process appropriately even if the patient moves to the limited areas during the movement of the bed.

Further, in the above embodiments, though for description convenience the first embodiment (the second embodiment) was described on the assumption that a urethane mattress is used and the third embodiment was described on the assumption that an air mattress is used, it is of course that the type of mattress is not be limited. That is, an air mattress may be used in the first embodiment (the second embodiment), whereas a urethane mattress may be used in the third embodiment.

DESCRIPTION OF REFERENCE NUMERALS

1 Bed Device
100 Controller
110 Status Detector
120 Position Detector
130 Operation Section
140 Notifying Unit
150 Bed Controller
160 Storage
162, 164, 166 Control Table

The invention claimed is:

1. A bed device comprising:
a memory configured to store a plurality of regulation contents, the regulation contents including a first status of the bed device, the first status being stored in association with a first input corresponding to a first regulated movement of the bed device; and
a controller configured to control movement of the bed in response to receipt of an input from a user and in association with the regulation contents stored in said memory and a current status of the bed device such that when the input received from the user is the first input, the controller is configured to regulate a movement of the bed device corresponding to the first regulated movement if the bed device is in the first status, and the controller is configured not to regulate a movement of the bed device corresponding to the first regulated movement if the bed device is not in the first status.

2. The bed device according to claim 1, wherein the regulation contents further including a second status of the bed device, the second status being stored in association with a second input corresponding to a second regulated movement of the bed device, and the second status being different from the first status.

3. The bed device according to claim 2, wherein the first regulated movement is different from the second regulated movement.

4. The bed device according to claim 1, wherein the first status is an edge-sitting mode in which the bed device takes a form that allows the user to sit on an edge of the bed device, and the first regulated movement is raising an upper leg of the user lying on the bed device.

5. The bed device according to claim 1, wherein the first status is a transferring mode in which the bed device takes a form that allows the user to transfer, and the first regulated movement is raising a back of the user lying on the bed device.

6. The bed device according to claim 1, wherein the first status is a status that an angle of a back portion of the bed device exceeds a first angle, and the first regulated movement is a rolling movement of the bed device.

7. The bed device according to claim 1, wherein when the first input is received, the controller is configured to suspend a movement of the bed device corresponding to the first input if the bed device is in the first status.

8. The bed device according to claim 7, further comprising a notifying means configured to notify an alert, and
wherein the notifying means notify the alert when suspending the movement of the bed device corresponding to the first input.

9. The bed device according to claim 8, wherein the notifying means is a display to notify that the movement of the bed device corresponding to the first input is regulated.

10. The bed device according to claim 9, wherein the display is configured to ask the user for confirmation when notifying that the movement of the bed device corresponding to the first input is regulated.

11. The bed device according to claim 10, wherein after the confirmation is checked by the user, the suspending of the movement of the bed device corresponding to the first input is released.

12. A bed device comprising:
a memory configured to store a plurality of regulation contents, the regulation contents including a first status of the bed device, the first status being stored in association with a first input corresponding to a first regulated movement of the bed device, the first status causing the controller to control a movement of the bed device so that the bed device takes a first form; and a controller configured to control movement of the bed in response to receipt of an input from a user and in association with the regulation contents stored in said memory and a current status of the bed device such that when the input received from the user is the first input, the controller is configured to regulate a movement of the bed device corresponding to the first regulated movement if the bed device is in the first status, and the controller is configured not to regulate a movement of the bed device corresponding to the first regulated movement if the bed device is not in the first status.

13. The bed device according to claim 1, wherein the regulation contents further including a second status of the bed device, the second status being stored in association with a second input corresponding to a second regulated movement of the bed device, and the second status being different from the first status.

14. The bed device according to claim 2, wherein the first regulated movement is different from the second regulated movement.

15. The bed device according to claim 1, wherein the first status is an edge-sitting mode in which the bed device takes a form that allows the user to sit on an edge of the bed device, and the first regulated movement is raising an upper leg of the user lying on the bed device.

16. The bed device according to claim 1, wherein the first status is a transferring mode in which the bed device takes a form that allows the user to transfer, and the first regulated movement is raising a back of the user lying on the bed device.

* * * * *